(12) United States Patent
Chevallet

(10) Patent No.: US 7,588,722 B2
(45) Date of Patent: Sep. 15, 2009

(54) EXTRACORPOREAL TREATMENT DEVICE WITH AUTOMATIC EMPTYING OF WASTE BAG

(75) Inventor: Jacques Chevallet, Serezin du Rhone (FR)

(73) Assignee: Gambro Lundia AB (SE)

( * ) Notice: Subject to any disclaimer, the term of this patent is extended or adjusted under 35 U.S.C. 154(b) by 265 days.

(21) Appl. No.: 10/873,191

(22) Filed: Jun. 23, 2004

(65) Prior Publication Data
US 2004/0267183 A1 Dec. 30, 2004

Related U.S. Application Data

(60) Provisional application No. 60/492,758, filed on Aug. 6, 2003.

(30) Foreign Application Priority Data
Jun. 25, 2003 (FR) .................. 03 07643

(51) Int. Cl.
*A61M 1/00* (2006.01)
*A61M 37/00* (2006.01)
*B01D 35/14* (2006.01)
*B01D 21/30* (2006.01)
*C02F 1/44* (2006.01)

(52) U.S. Cl. .................. 422/44; 604/6.01; 210/86; 210/134; 210/321.65

(58) Field of Classification Search ............. 422/44–48; 604/4.01–6.16; 210/86, 104, 134, 137, 116, 210/257.2, 321.2, 321.3, 321.65
See application file for complete search history.

(56) References Cited

U.S. PATENT DOCUMENTS
3,888,126 A 6/1975 Cross
(Continued)

FOREIGN PATENT DOCUMENTS
DE 33 18 120 11/1983
(Continued)

OTHER PUBLICATIONS

International Preliminary Report on Patentability for International Application No. PCT/IB2004/002024.

*Primary Examiner*—Leslie R Deak
*Assistant Examiner*—Philip R Wiest
(74) *Attorney, Agent, or Firm*—Finnegan, Henderson, Farabow, Garrett & Dunner L.L.P.

(57) ABSTRACT

The invention relates to a blood treatment device by extracorporeal circulation comprising a filter having a primary chamber and a secondary chamber separated by a semi-permeable membrane; a blood circuit comprising an arterial line intended to come from the patient, the filter's primary chamber and the venous line intended to return to the patient; a dialysate circuit comprising the filter's secondary chamber and at least a drain line for circulating the waste intended to come from the filter and intended to go to a drain; a first bag in fluid communication with the drain line; at least a first gravimetric weighing means linked to the first bag, fluid flow rate adjustment means acting on the drain line; a control unit linked to the first gravimetric weighing means and with the fluid flow rate adjustment means; a second bag in fluid communication with the drain line, the control unit being capable of receiving weight signals from the first gravimetric weighing means and of controlling the fluid flow rate adjustment means to load one of the bags with liquid while the other bag unloads liquid, and vice-versa.

The invention also relates to a single-use drain line for use in a treatment device according to the invention.

29 Claims, 10 Drawing Sheets

U.S. PATENT DOCUMENTS

| | | |
|---|---|---|
| 4,267,041 A | 5/1981 | Schael |
| 4,372,846 A | 2/1983 | Yamagami et al. |
| 4,713,171 A | 12/1987 | Polaschegg |
| 4,769,132 A * | 9/1988 | Patono .................. 210/86 |
| 4,859,319 A * | 8/1989 | Borsari .................. 210/86 |
| 4,894,150 A | 1/1990 | Schurek et al. |
| 4,994,026 A | 2/1991 | Fecondini |
| 5,043,074 A | 8/1991 | Chevallet |
| 5,441,636 A * | 8/1995 | Chevallet et al. ............ 210/232 |
| 5,650,071 A | 7/1997 | Brugger et al. |
| 5,672,481 A * | 9/1997 | Minshall et al. ............ 435/7.21 |
| 5,725,775 A * | 3/1998 | Bene et al. ................ 210/646 |
| 5,993,657 A | 11/1999 | Williams et al. |
| 6,039,877 A * | 3/2000 | Chevallet et al. ............ 210/636 |
| 6,042,784 A | 3/2000 | Wamsiedler et al. |
| 6,561,996 B1 | 5/2003 | Gorsuch |
| 6,561,997 B1 * | 5/2003 | Weitzel et al. ............ 604/6.09 |
| 6,818,179 B1 * | 11/2004 | Edgson et al. ............ 422/38 |
| 7,153,286 B2 * | 12/2006 | Busby et al. ............ 604/6.11 |
| 2004/0167457 A1 * | 8/2004 | Tonelli et al. ............ 604/6.09 |

FOREIGN PATENT DOCUMENTS

| | | |
|---|---|---|
| DE | 38 01 316 | 7/1988 |
| DE | 94 03 081.2 | 6/1994 |
| DE | G 94 03 081.2 | 6/1994 |
| EP | 0 213 050 | 3/1987 |
| EP | 0 722 744 | 7/1996 |
| EP | 0 796 997 | 9/1997 |
| EP | 0 796 997 A1 * | 9/1997 |
| EP | 796997 * | 9/1997 |
| FR | 765258 | 12/1933 |
| FR | 2472936 | 7/1981 |
| FR | 2594340 | 8/1987 |
| JP | 53 083397 | 7/1978 |
| JP | 59 037959 | 3/1984 |
| WO | WO 99/19007 | 4/1999 |

* cited by examiner

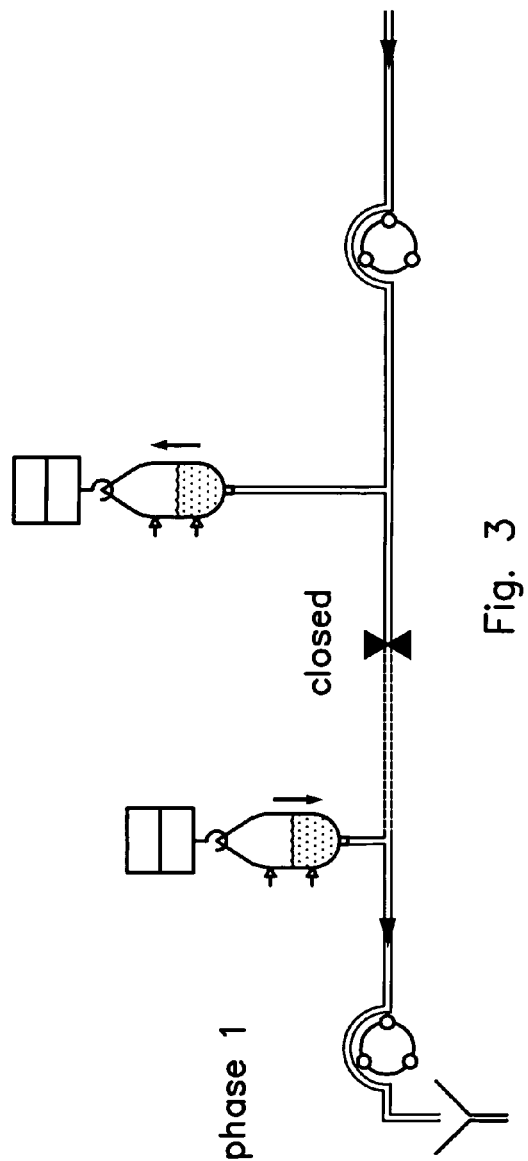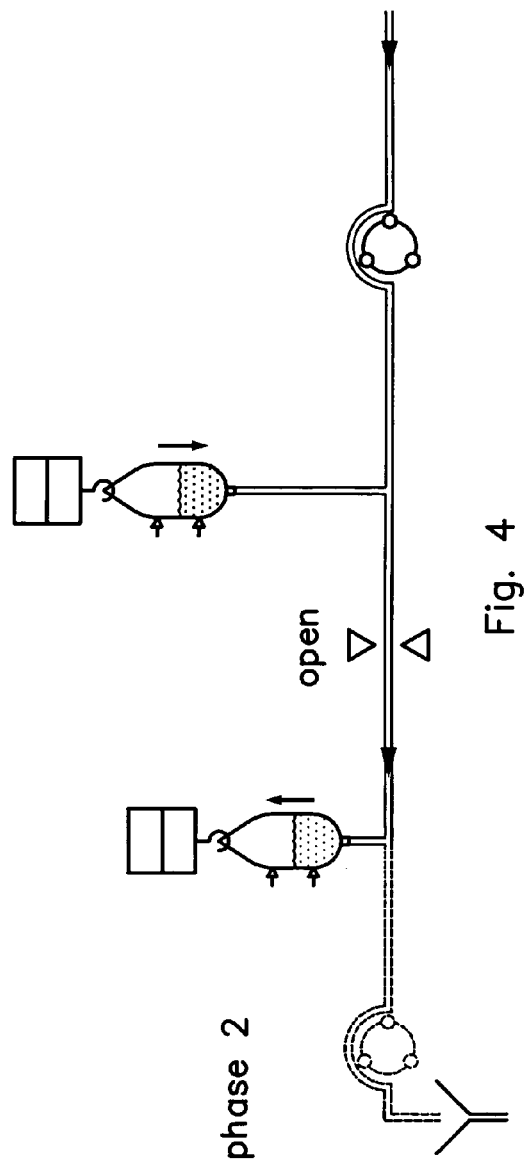

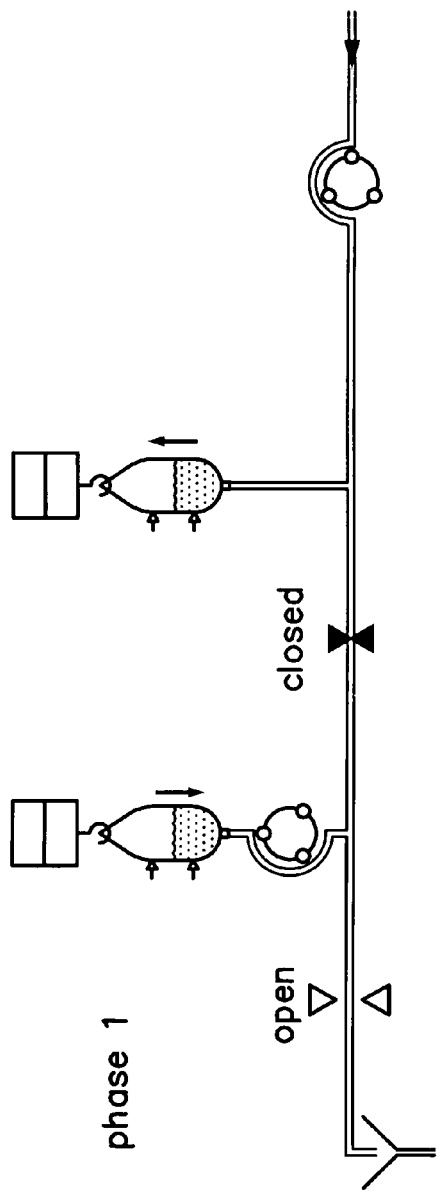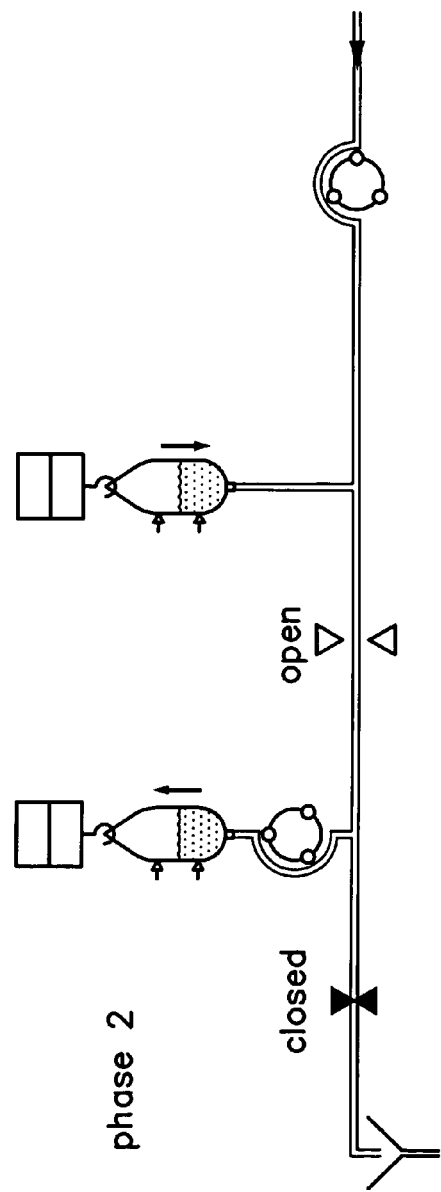
phase 1
closed
open
Fig. 7
phase 2
open
closed
Fig. 8

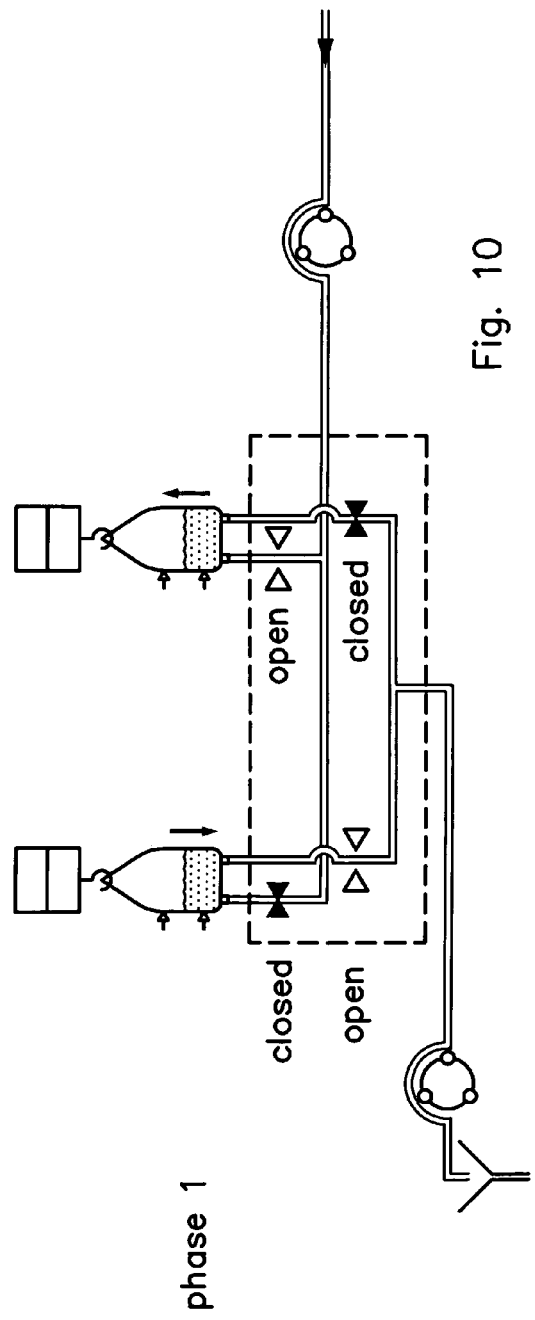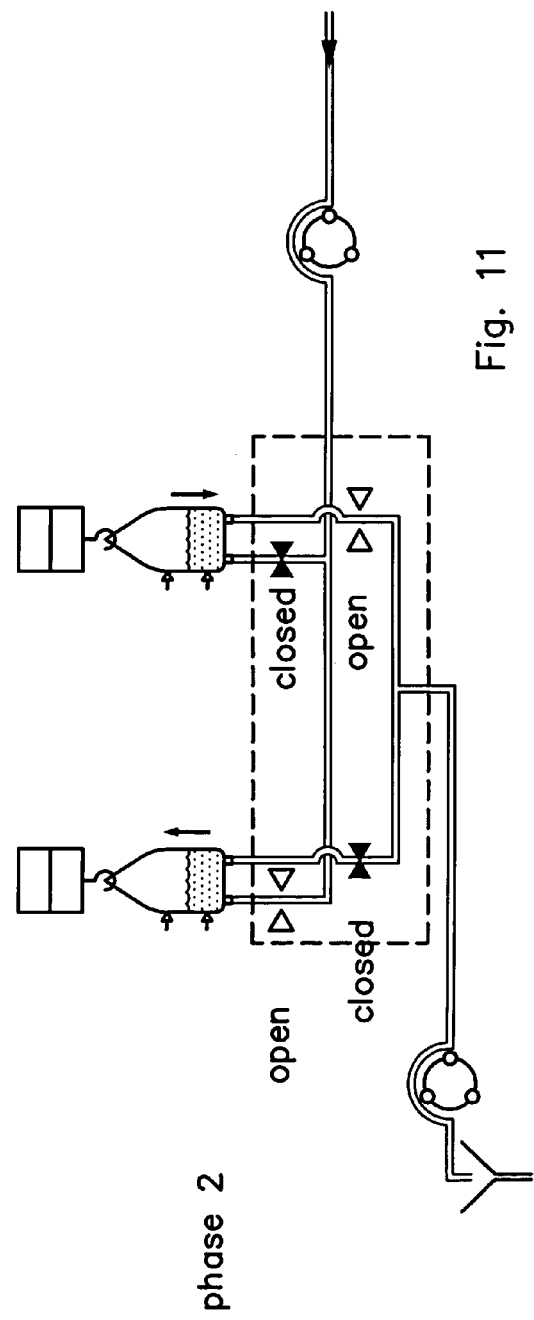

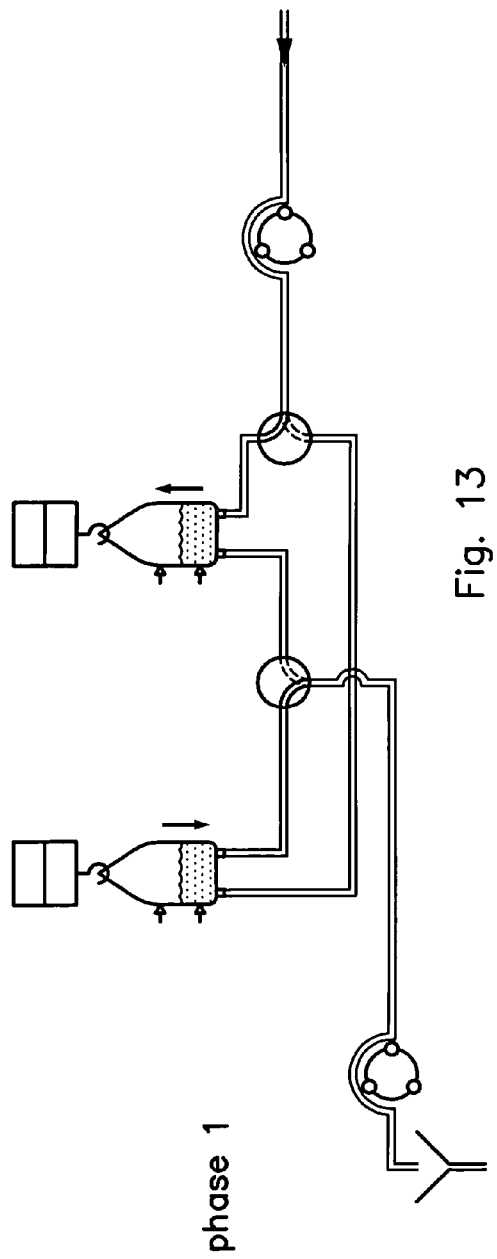
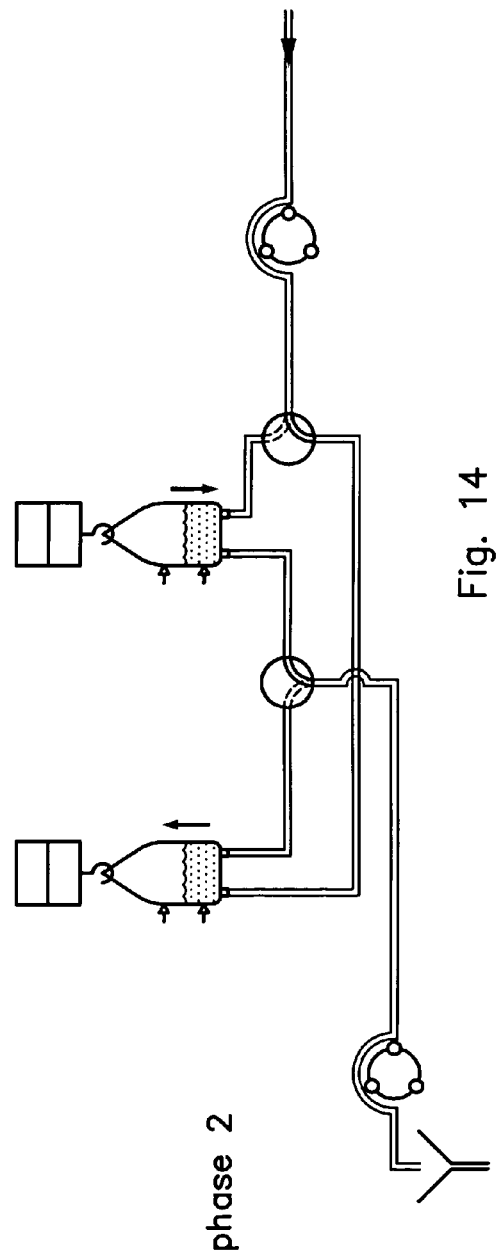
phase 1　　　Fig. 13
phase 2　　　Fig. 14

EXTRACORPOREAL TREATMENT DEVICE WITH AUTOMATIC EMPTYING OF WASTE BAG

CROSS REFERENCE TO RELATED APPLICATIONS

This application claims priority of French patent application No 03 07643, filed on Jun. 25, 2003 and the benefit of U.S. Provisional Application No. 60/492,758, filed on Aug. 6, 2003, the contents of which are incorporated herein by reference.

TECHNICAL FIELD OF THE INVENTION

The present invention relates to extracorporeal blood treatment, and more particularly to an innovative and improved device for treating blood in which waste is drained automatically.

STATE OF THE PRIOR ART

Extracorporeal blood treatment means taking the blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment is used with patients incapable of effectively eliminating matter from their blood, for example in the case of a patient who is suffering from temporary or permanent kidney failure. These and other patients may undergo extracorporeal blood treatment to add to or to eliminate matter from their blood, to maintain an acid-base balance or to eliminate excess body fluids, for instance.

Extracorporeal blood treatment is typically performed by sampling the patient's blood in a continuous flow, by introducing the blood into a primary chamber of a filter in which the blood goes through a semi-permeable membrane. The semi-permeable membrane selectively lets the unwanted matter contained in the blood pass through the membrane, from the primary chamber to the secondary chamber, and also selectively lets the beneficial matter contained in the liquid going into the secondary chamber pass through the membrane to the blood going into the primary chamber, according to the type of treatment.

A number of extracorporeal blood treatments can be performed by the same machine. In ultrafiltration (UF) treatment, the unwanted matter is eliminated from the blood by convection through the membrane in the secondary chamber.

In hemofiltration (HF) treatment, the blood runs through the semi-permeable membrane as in UF, and the beneficial matter is added to the blood, typically by the introduction of a fluid into the blood, either before, or after its passage through the filter and before it is returned to the patient.

In hemodialysis (HD) treatment, a secondary fluid containing the beneficial matter is introduced into the filter's secondary chamber. The blood's unwanted matter crosses the semi-permeable membrane and penetrates into the secondary fluid, and the beneficial matter of the secondary fluid can cross the membrane and penetrate into the blood.

In hemodiafiltration (HDF) treatment, the blood and the secondary fluid exchange their matter as in HD, and further, matter is added to the blood, typically by introducing a fluid into the treated blood before it is returned to the patient as in HF, and unwanted matter are also eliminated from the blood by convection.

In each treatment, the secondary fluid goes through the filter's secondary chamber and receives the blood's unwanted matter by means of the membrane. This liquid is then extracted from the filter: it is commonly called waste, and is sent to a drain or to a receptacle then intended to be discharged into a drain.

As described above, a patient may suffer from temporary or permanent kidney failure.

In the case of permanent kidney failure, the patient has to undergo regular sessions, for instance three times a week, of extracorporeal blood treatment with a relatively high blood extraction rate, i.e. between 200 and 500 ml/min.

Generally, health care personnel can install the treatment device with online liquid preparation that can include online sterilization, and can install an online drain.

In the area of temporary kidney failure, the patient has to be treated urgently and has to undergo continuous and long-term extracorporeal blood treatment with a relatively low blood extraction rate, i.e. between 100 and 200 ml/min.

Net water extraction from the patient is limited because the emergency treated patient is in a critical state. In this emergency treatment case, health care personnel have to act rapidly and thus do not have the time to install the treatment apparatus with online liquid preparation. Indeed, it is much faster to attach to the device a dialysis liquid and/or an infusion liquid already prepared and stored in a sterile single-use bag, and it is faster to attach an empty single-use bag to collect the waste.

A machine using this solution of sterile single-use bags is known. During the intensive kidney-failure treatment session, this extracorporeal treatment machine has to provide and control several flow rates:

the infusion flow rate (Dinf), if liquid infusion with beneficial matter is prescribed for the patient, the dialysis liquid flow rate (Ddial) entering into the filter's secondary chamber for HF or HDF modes, the flow rate representing the patient's weight loss (Dwloss), i.e. the quantity of liquid extracted and lost by the patient, the flow rate representing the waste coming from the filter (Dwaste).

The system represented by the patient and the blood treatment apparatus is a closed system. Thus the following equation may be deduced:

$$D\text{waste} = D\text{inf} + D\text{dial} + D\text{wloss} \tag{1}$$

Also, before the treatment session, the doctor may prescribe:

the infusion flow rate Dinf to control the quantity of beneficial matter to be infused to the patient, the dialysis flow rate Ddial to control matter going through the filter, the patient's weight loss flow rate Dwloss to prevent any potential illness of the patient during the session.

Consequently the waste flow rate is calculated using the equation (1).

For this, the use of a sterile single-use bag that enables the waste to be received and collected was described above. This known use is illustrated in FIG. 1. The bag 11 is connected to the end of the waste line 8 linked to the secondary chamber 4. This bag 11 is combined with a gravimetric weighing means 21 linked to a control unit 41. Thus, weight signals are transmitted to the control unit 41 that is capable of monitoring the weight changes of the bag linked to the waste flow rate through the waste line 8, and to control a pump 31 acting on the waste line.

However, the session can last several days and the single-use waste bag is filled well before the end of the session. This phenomenon is all the more pronounced during an intensive treatment. Indeed, one wishes both to exchange a large quantity of liquid in HF or HDF therapy, and to perform long-term treatments.

As soon as the bag reaches a set filling level, the doctor or nurse acts on the machine to temporarily stop the pumps acting on the waste line, on the dialysis liquid line and on the infusion line respectively, while the blood continues to circulate extracorporeally in the filter's primary chamber. Once the pumps are stopped, the user has to disconnect and unhook the filled waste bag, drain it and/or clear it to the drains network. Then the user attaches and connects a new empty single-use bag to the treatment device and restarts the pumps to return to the extracorporeal treatment with fluid circulation through the two chambers (3, 4) of the filter 2.

This bag replacement operation has disadvantages:
- on the one hand, it can last several minutes and extend the treatment time by several minutes whenever the bag is filled and needs changing,
- on the other hand, this bag changing operation is performed while the blood still flows in the blood circuit without being able to come into contact with a flowing dialysis liquid, so that the treatment quality is then lessened,
- also, this operation is performed by health care personnel who have to monitor several patients at the same time. A waiting time before action by the personnel can again be added to the treatment time,
- further, the regular changing of the drain bag during a session adds an economic cost to the treatment,
- finally, bags generally have a volume of about five liters, are heavy and relatively fragile objects to handle and contain waste that may be a source of unwanted substances if the bag were inconveniently to be perforated while handling.

DESCRIPTION OF THE INVENTION

The present invention is described with particular reference to the intensive kidney failure treatment (also called acute kidney failure treatment), without thereby limiting the scope of the invention to this specific application.

The object of the invention is to provide an extracorporeal blood treatment device having the same functions as currently known devices and enabling the described problems to be solved.

The object of the invention is to provide a blood treatment device for automatic draining and for waste flow rate control, a single-use drain line intended to work together with such a device as well as a corresponding draining method.

The blood treatment device by extracorporeal circulation according to the invention comprises:
- a filter having a primary chamber and a secondary chamber separated by a semi-permeable membrane,
- a blood circuit having an arterial line intended to draw blood from a patient, the filter's primary chamber and a venous line intended to return blood to the patient,
- a dialysate circuit comprising the filter's secondary chamber and at least one drain line for directing to a drain the waste liquid coming from the filter's secondary chamber,
- a first bag in fluid communication with the drain line,
- at least one first gravimetric weighing means linked to the first bag,
- fluid flow rate adjustment means acting on the drain line,
- a control unit linked to the first gravimetric weighing means and to the fluid flow rate adjustment means, wherein the blood treatment device comprises:
- a second bag in fluid communication with the drain line, and wherein the control unit is capable of:
- receiving the weight signals from the first gravimetric weighing means and,
- controlling the fluid flow rate adjustment means to load one of the bags with liquid while the other bag unloads liquid, and vice-versa.

The single-use line for use in the device according to the invention comprises:
- a drain line connecting the filter output to the drain,
- fluid flow rate adjustment means on the drain line,
- two bags each attached to the drain line and intended to be attached to the treatment apparatus,
- at least one first part of the drain line intended to work together with a peristaltic pump.

BRIEF DESCRIPTION OF THE DRAWINGS

Additional characteristics and advantages will appear with the detailed description of a preferred but not exclusive embodiment of an extracorporeal blood treatment device according to the invention. This description will be given below with reference to the annexed drawings, which are supplied for information purposes and are thus not limiting.

Four embodiments of the invention are described.

FIG. 3 represents a first operating phase of the first embodiment of the device according to the invention.

FIG. 4 represents the second operating phase of the first embodiment of the device according to the invention.

FIG. 7 represents the first operating phase of the second embodiment of the device according to the invention.

FIG. 8 represents the second operating phase of the second embodiment of the device according to the invention.

FIG. 10 represents the first operating phase of the third embodiment of the device according to the invention.

FIG. 11 represents the second operating phase of the third embodiment of the device according to the invention.

FIG. 13 represents the first operating phase of the fourth embodiment of the device according to the invention.

FIG. 14 represents the second operating phase of the fourth embodiment of the device according to the invention.

DETAILED DESCRIPTION OF THE EMBODIMENTS OF THE INVENTION

Description Common to All Embodiments

Figure 1:
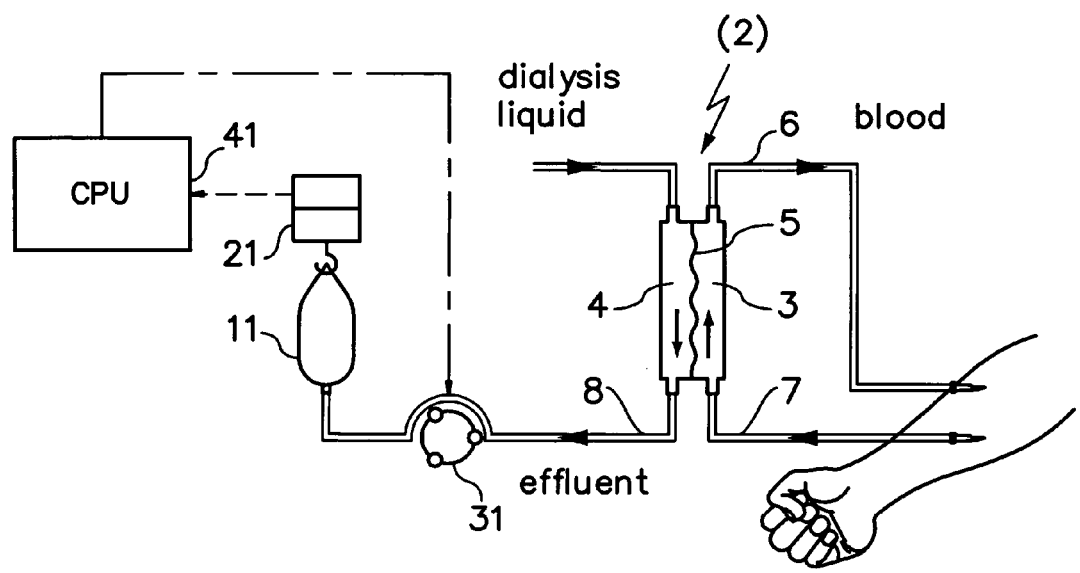
FIG. 1 represents an extracorporeal blood treatment device according to the known state of the art.

With reference to the appended figures, globally 1 designates the extracorporeal blood treatment device. The blood treatment device 1 represented in FIGS. 1, 2, 6, 9 and 12 is in an operational configuration that enables it to perform a hemodialysis treatment. The other treatment configurations mentioned previously (ultrafiltration, hemofiltration and hemodiafiltration) are of course transposable to the embodiments of the invention.

The devices according to the various embodiments of the invention represented in FIGS. 2, 6, 9 and 12 contain one filter 2 having a primary chamber 3 and a secondary chamber 4 separated by a semi-permeable membrane 5; a blood circuit comprises an arterial line 6 intended to draw blood from the patient, the filter's primary chamber 3 and a venous line 7 intended to be returned blood to the patient; a dialysate circuit comprises the filter's secondary chamber 4 and at least one drain line 8 for directing to a drain the waste liquid coming from the filter's secondary chamber, a first bag 11 with fluid connection to the drain line 8, at least one first means of gravimetric weighing 21 linked to the first bag 11, means of adjusting the fluid flow (31, 32, 33, 34) acting on the drain line 8; a control unit 41 is linked to the first means of gravimetric weighing 21 and to the fluid flow adjustment means (31, 32, 33, 34). The devices according to the various embodiments of the invention comprise a second bag 12 with fluid communication to the drain line 8.

The control unit 41 is capable of receiving the weight signals from the first gravimetric weighing means and of controlling the fluid flow adjustment means (31, 32, 33, 34) to load one of the bags (11, 12) with liquid while the other bag (12, 11) unloads liquid, and vice-versa.

In all embodiments, the control unit 41 is also capable of calculating, from the received weight signals, the amount of liquid coming from the filter and entering the drain line 8.

More particularly and in all embodiments, the adjustment means comprises a first adjustment organ 31 acting upstream of the two bags (11, 12). Thus the first organ acts on the drain line, after the filter's secondary chamber outlet, upstream of the bags. Also the control unit 41 will be programmed to control the first adjustment organ 31 to ensure the presence of a substantially continuous flow during the treatment. Indeed, the flow adjustment means are controlled so as not to have to stop the flow of waste coming from the filter. For better treatment quality, it can be ensured that the flow rate of the measured waste stays substantially constant or follows a required profile during the session.

In all embodiments, the adjustment means can comprise a second adjustment organ 32 acting between the two bags (11, 12).

In all embodiments, the adjustment means can comprises a second adjustment organ 33 acting between the two bags (11, 12).

Additional characteristics are possible for all embodiments.

Thus, the device can comprise a second gravimetric weighing means 22 linked to the second bag 12 and connected to the control unit 41. Indeed, the weight information supplied to the control unit by the first gravimetric weighing means has the function of knowing the weight of the single-use bag so as both to know the amount of liquid flowing, and to control the loading and unloading phase of the two bags by using two threshold values—maximum and minimum—set by the user according to the bag's volume.

A second gravimetric weighing means can be linked to the second bag. The first function of the second gravimetric weighing means is to know the weight of the liquid flowing. It can also be used to the control the cyclic loading and unloading process by using one or two threshold values of the second gravimetric weighing means, together with one or two threshold values of the first gravimetric weighing means. But if the use of the two threshold values is enough for the draining control, the four threshold values of the two scales can be used for preventive alarm purposes concerning a bag's abnormal state.

In all embodiments, the control unit 41 is capable of calculating the amount of fluid coming from the filter 2 and entering the drain line 8 from the weight signals received from the first gravimetric weighing means 21 and/or the second gravimetric weighing means 22.

For all embodiments, the control unit 41 is capable of activating a control procedure having two alternating phases.

In a first phase, the control unit controls the actual flow rate of the adjustment means (31, 32, 33, 34) according to the required flow rate profile and the weight information coming from at least the first gravimetric weighing means 21.

In a second phase, the control unit 41 controls the actual flow rate of the adjustment means (31, 32, 33, 34) according to the required flow rate profile and the weight information coming from the first and second gravimetric weighing means (21, 22).

The control unit 41 is also capable of activating a control procedure comprising two alternated phases with a control of the actual flow rate of the adjustment means (31, 32, 33, 34) during the first phase which is also performed according to the weight information of the second gravimetric weighing means 22. This alternative can be used in the third and fourth embodiments.

In all the embodiments, the control unit 41 is capable of receiving the weight information from the first gravimetric weighing means 21 and/or the second gravimetric weighing means 22, calculating the actual flow rate of the fluid coming from the filter 2 and comparing it with a required set flow rate or with a flow rate profile required by the user, controlling the fluid's actual flow rate using the adjustment means to best approach the required flow rate profile of fluid coming from the filter 2.

In all the embodiments, the control unit is capable of receiving the weight information from the first gravimetric weighing means 21 and/or from the second gravimetric weighing means 22, independently determining the filling status of each bag, and controlling, from the filling status of each bag, an alternating and successive bag loading and unloading procedure.

In all the embodiments, the control unit is capable of receiving the weight information from the first gravimetric weighing means 21 and/or from the second gravimetric weighing means 22, detecting the maximum and minimum threshold values for each of the bags $P_{1mini}$, $P_{1maxi}$, $P_{2mini}$, $P_{2maxi}$, and controlling, from the threshold values, a bag loading and unloading procedure according to the following steps:

loading of one bag and unloading of the other bag,
detection of a limit threshold,
unloading of one bag and loading of the other bag,
detection of another limit threshold.

Description Common to the First and Second Embodiments

In the first two embodiments of the invention, the drain line 8 can be defined with several components: a conduit 80 connecting the filter 2 to the drain 9, a first branch 81 connecting the first bag 11 to the conduit 80, a second branch 82 connecting the second bag 12 to the conduit 80. The second branch 82 is connected to the conduit 80 upstream of the first branch 81. Also the first adjustment organ 31 and the second adjustment organ 32 act on the conduit 80, and not on the two branches.

Each of two branches can comprise a line with two respective terminal connections (811, 812, 821, 822), or a direct connection between the drain line (80) and an opening of a bag.

Description of the First Embodiment

Figure 2:
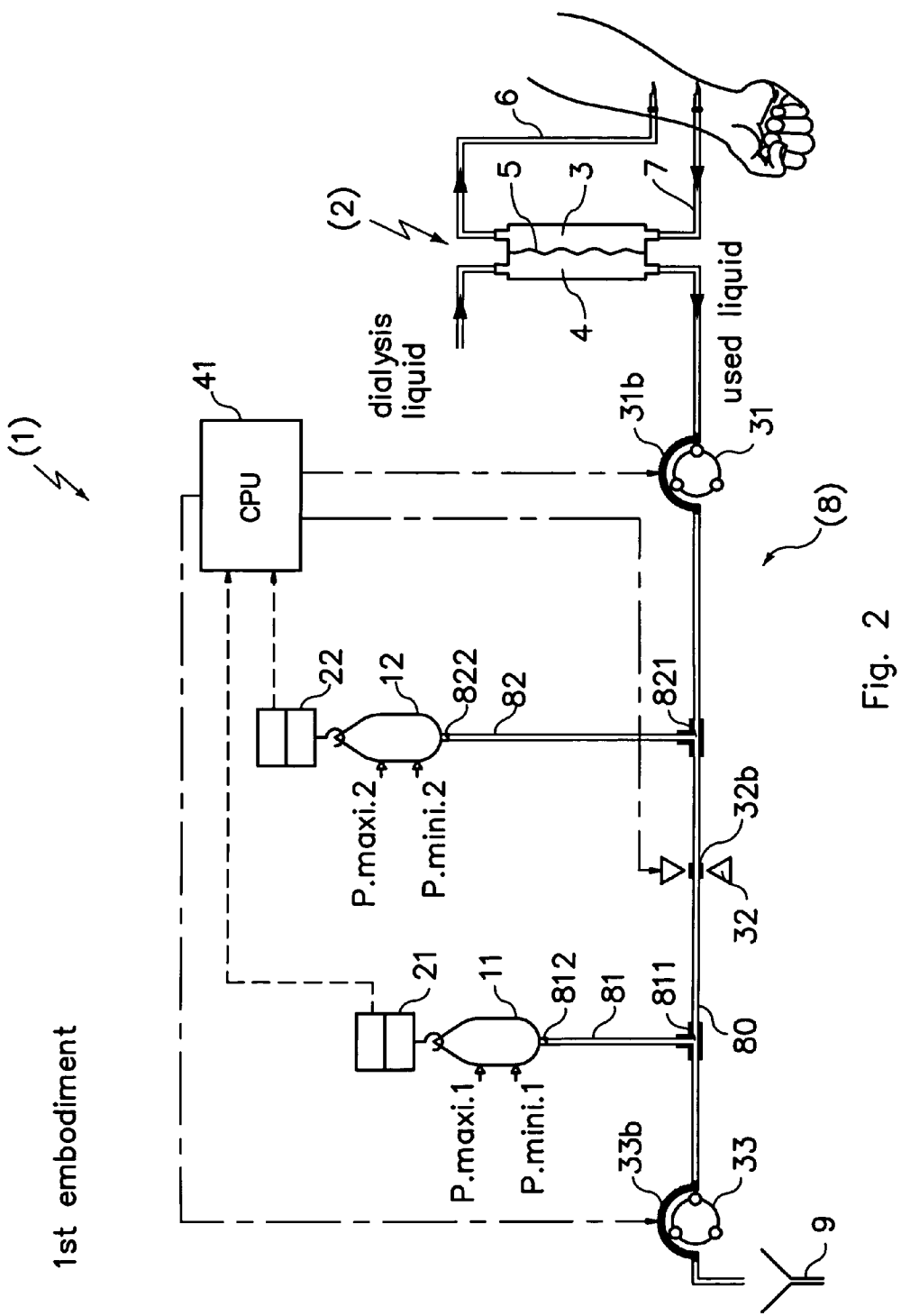
FIG. 2 represents a first embodiment of the device according to the invention.

In the first embodiment shown in FIG. 2, the first 31 and third 33 adjustment organs are conveniently the peristaltic pumps, and the second adjustment organ 32 is a valve.

In the first embodiment shown in FIG. 2, the place in the bags' space has to be taken into account. It is known that the single-use bags used are attached to the machine with the opening of the bags placed conveniently towards the bottom to enable continuous flow of the fluid. One may have several bags especially a single-use bag collecting the waste, a single-use bag containing perfusion liquid, and a single-use bag comprising a dialysis liquid. These bags are often attached at the same level.

The invention uses gravity to facilitate the liquid's runoff without necessarily having to use an additional pump. Use is made of this in the first embodiment, but gravity could be used in the other embodiments by those skilled in the art using their knowledge and the description of the invention.

In this way, the first bag 11 is placed lower than the second bag 12 on the machine. Consequently, when waste is taken from the filter's secondary chamber and fluid flow is possible between the two bags, the first bag 11 will be loaded in priority in relation to the second bag, even if the second bag is placed upstream of the first bag in the fluid's circulation direction. Similarly, when the second bag is filled and the second is substantially empty, the second bag 12 will unload into the first bag 11 by gravity.

FIGS. 3 and 4 show the two operating phases of the drain cycle used by the apparatus and the fluid flow directions in the drain line, for the first embodiment.

Indeed, the control unit 41 is capable of controlling the adjustment organs (31, 32, 33) according to two alternated steps.

In a first step, the control unit 41 controls the opening of the second adjustment organ 32 and the stopping of the third adjustment organ 33 to load the second bag 12 and unload the first bag 11 into the drain 9.

In a second step, the control unit 41 controls the opening of the first adjustment organ 31 and the stopping of the third adjustment organ 33 to unload the second bag 12 and load the first bag 11.

It will be noted that the control to go from one phase to the other has to be performed conveniently and simultaneously in order to have a better treatment quality, but a small time gap may be noticed between two actions, for instance between the opening of the second adjustment organ 32 and the stopping of the third adjustment organ 33. This is valid for any control of any adjustment means.

Figure 5:
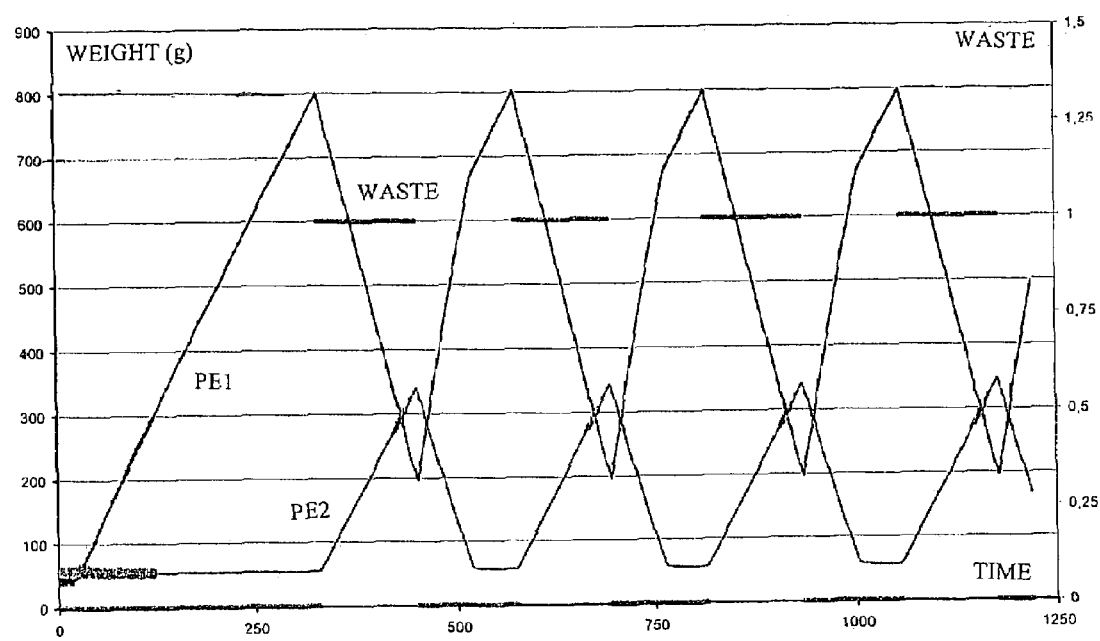
FIG. 5 represents the weight change of bags measured during the treatment session of the first embodiment.

FIG. 5 represents, for the first embodiment, the weight change of each bag according to the treatment time. These measurements were made experimentally and are reproducible.

The succession of the two phases or steps during the draining cycle, preceded by a system-priming phase will now be explained, starting from the particular example of FIG. 5.

At the start of the session, the two bags are almost empty (a weight of 50 g is recorded) and a priming phase is implemented.

The control unit primes the first adjustment means 31, opens the second adjustment organ 32, and does not operate the third adjustment means 33.

The first adjustment organ controls the waste flow in the drain line 8. From then, the liquid goes into the conduit 80.

Now the first bag 11 is downstream in relation to the second bag 12, but is attached to the device lower than the second bag. More especially, the top limit of the first bag is placed lower or at the same level as the bottom limit of the second bag. The second bag is loaded in priority in relation to the first bag. Thus, it may be seen that the weight of the first bag 11 (PE1 on FIG. 5) increases regularly in priority in relation to the weight of the second bag 12 (PE2 on FIG. 2), which remains unchanged.

As soon as the first bag 11 reaches a maximum set weight $P_{1max}$ (800 g for the test), the device will operate according to a first phase: The first adjustment organ 31 continues to operate, the second adjustment organ 32 is closed and the third adjustment organ operates to conduct the liquid to the drain.

From then the first bag 11 whose weight will have been memorized by the control unit, will unload into the drain (WASTE on FIG. 5). It may be seen that the weight of the first bag regularly decreases from 800 g to 200 g.

On the other hand, the second bag is loaded with the waste coming from the filter. A weight increase of the second bag 22 from 50 g to 330 g approximately can be seen.

This phase is performed until a minimum weight threshold of the first bag $P_{1mini}$ is reached (200 g), or a maximum weight threshold of the second bag $P_{2maxi}$ (330 g) is reached, or the first of the two above-mentioned thresholds is reached.

When such a threshold is detected, the control unit controls the entry into the second phase.

The unit 41 controls the opening of the second adjustment organ 32 and the stopping of operation of the third adjustment organ 33. Thus, the second almost full bag, whose weight information can be memorized by the control unit, unloads into the first almost empty bag. It can be seen that the first bag fills not only with the liquid contained in the second bag 22 but also with the liquid directly coming from the filter. That is why an inflection of the line representing the regular weight increase during the second phase can be seen: the second bag is almost emptied at this moment and the loading of the first bag will be performed less fast (50 g).

The first and second phase will alternate in this way until the end of the session.

The size of each of the bags, the size of the single-use lines is set by the user before the session. In the test carried out with the first embodiment, the second bag had a volume of about 500 g while the first bag had a bigger volume, about 1 kg; the lines have the same size. Naturally the flow rates adopted during the session match the size of the bags and the line and are such that the first bag 11 reaches a set minimum weight before the second bag 12 reaches a set maximum weight. In the illustrated test, the draining flow rate is 300 mL/min and the flow rate through the first adjustment organ is 150 mL/min.

Description of the Second Embodiment

Figure 6:
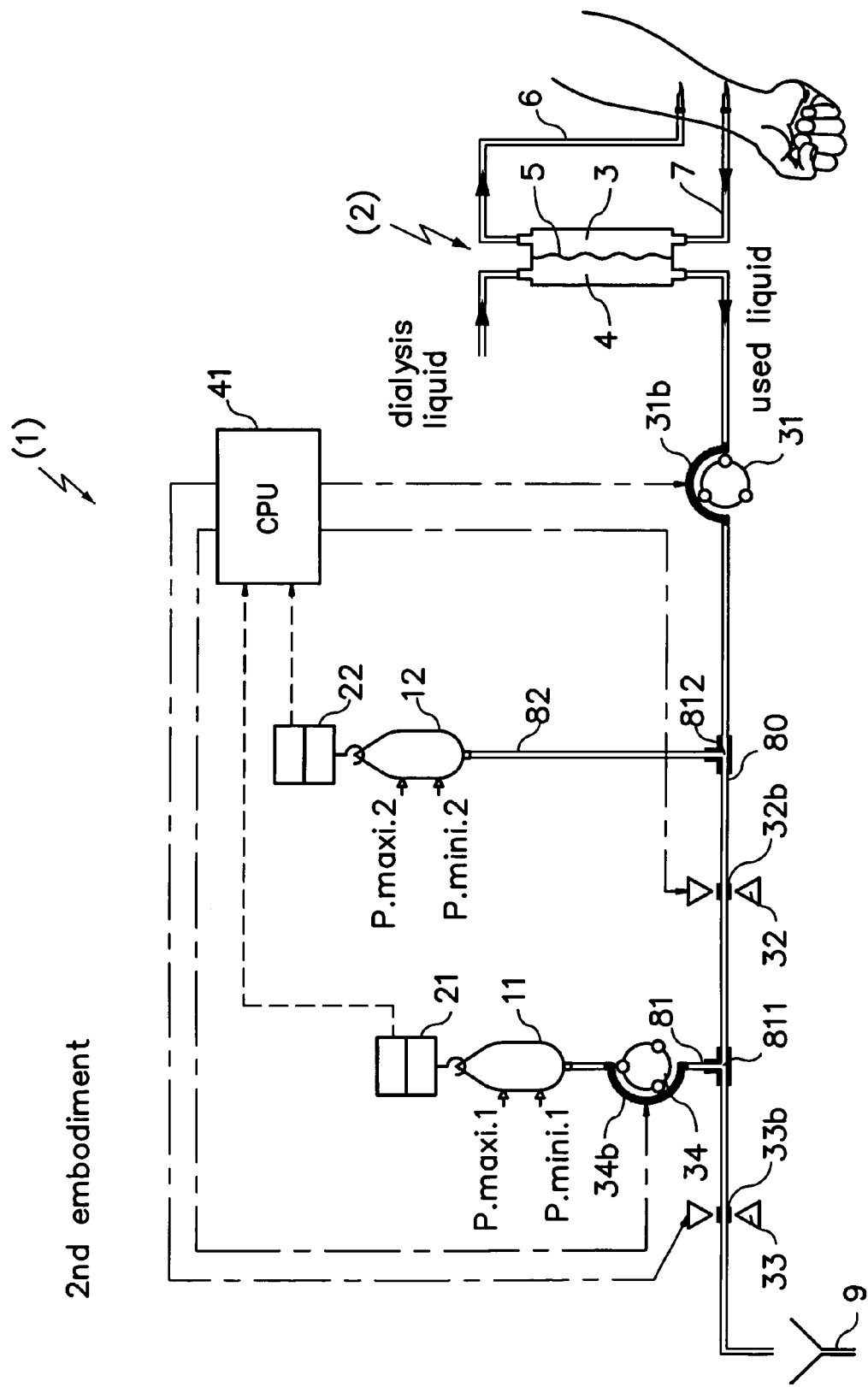
FIG. 6 represents a second embodiment of the device according to the invention.

A second embodiment is shown in FIG. 6 and the two operating phases are shown in FIGS. 7 and 8.

In the second embodiment, the adjustment means can comprise a fourth adjustment organ 34 acting on the first branch 81 between the two connections (811, 812).

This fourth adjustment organ 34 can comprise indifferently a pump, more particularly a peristaltic pump, a valve, more particularly a two-way clamp or a valve with adjustable opening.

More particularly in the second embodiment, the first and fourth adjustment organs (31, 34) can be peristaltic pumps and the second and third adjustment organs (32, 33) can be valves.

In the second embodiment, the control unit 41 is capable of controlling the flow rate adjustment means (31, 32, 33, 34) according to two alternating steps.

In first step, the control unit 41 controls the closing of the second adjustment organ 32, the opening of the third adjustment organ 33, the activation of the fourth adjustment organ 34 in the bag-to-conduit direction.

In the second step, the control unit 41 controls the opening of the second adjustment organ 32, the closing of the third adjustment organ 33, and the activation of the fourth adjustment organ 34 in the conduit-to-bag direction.

Description Common to the Third and Fourth Embodiments

Figure 9:
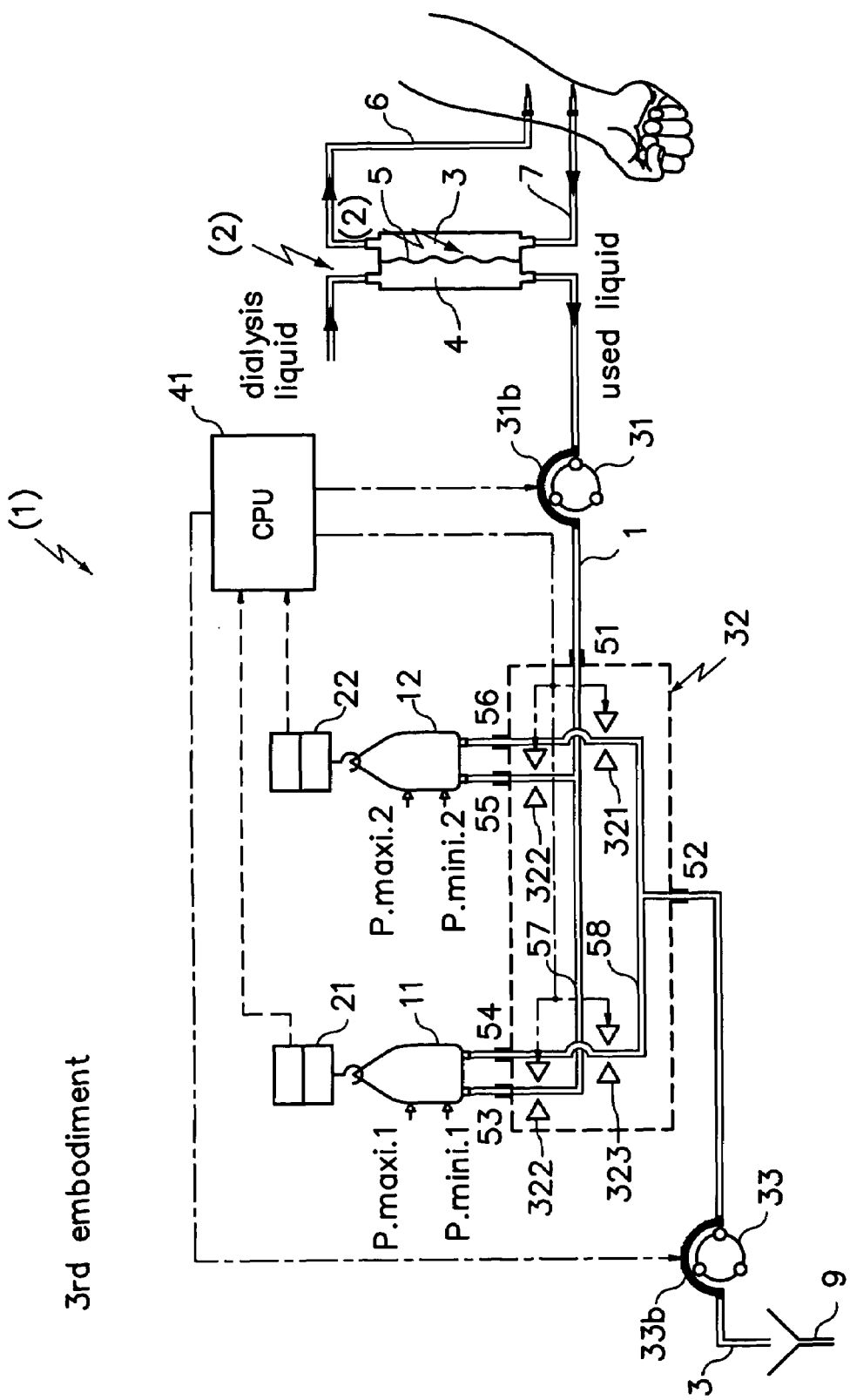
FIG. 9 represents a third embodiment of the device according to the invention.
Figure 12:
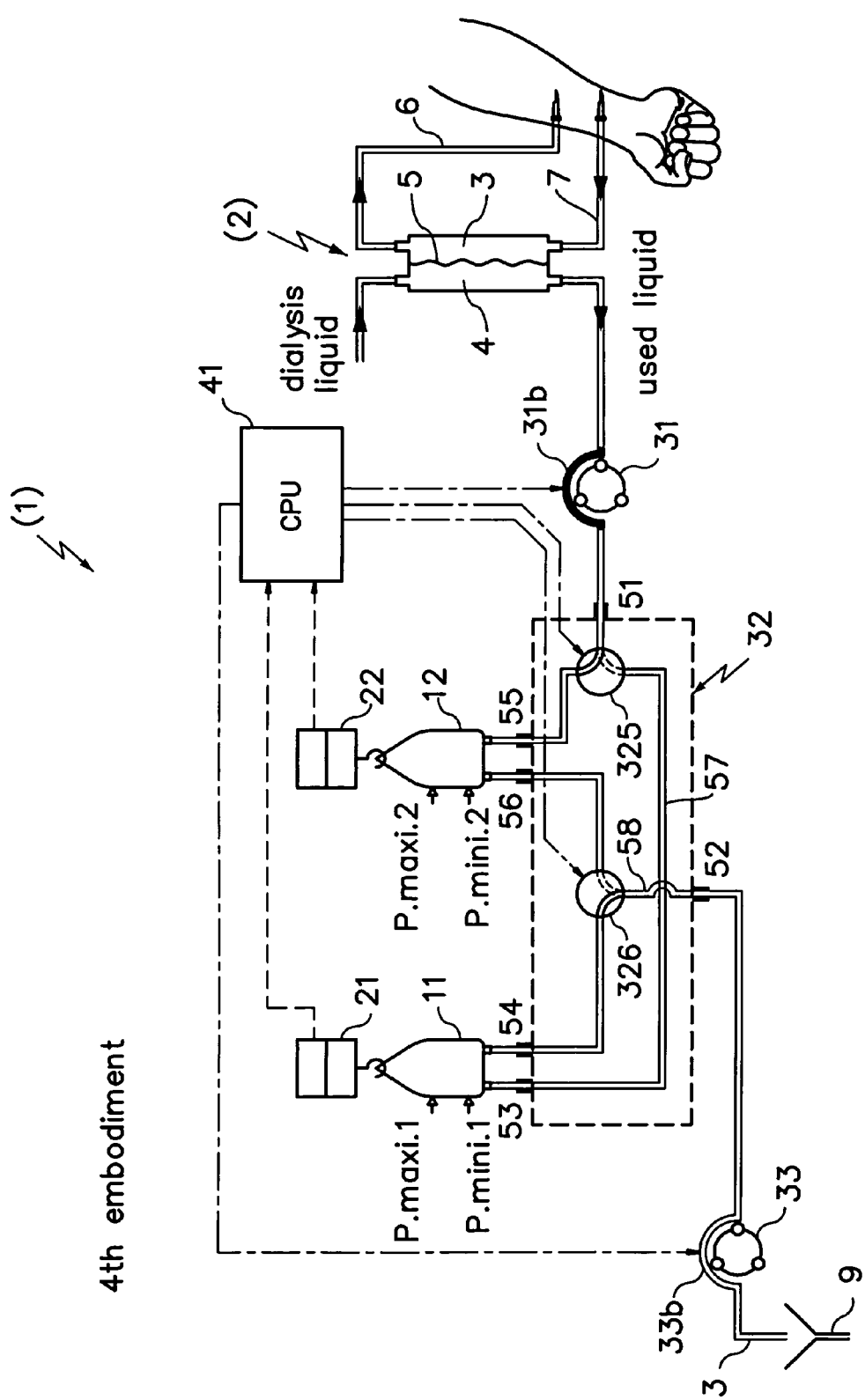
FIG. 12 represents a fourth embodiment of the device according to the invention.

The invention also comprises a third and fourth embodiment shown respectively in FIGS. 9 and 12 and whose two operating phases are shown respectively in FIGS. 10 and 11 as well as 13 and 14.

In these two embodiments, the second adjustment organ 32 comprises a hydraulic system having six ports (51, 52, 53, 54, 55, 56) distributed as follows:
- a first input port 51 in fluid communication with the input portion of the drain line 8 intended to be linked to the filter,
- a second input port 52 in fluid communication with the output portion of the drain line 8 intended to be linked to the drain,
- a third input port 53 and a fourth output port 54 each in fluid communication with the first bag 11,
- a fifth input port 55 and a sixth output port 56 each in fluid communication with the second bag 12,

Description of the Third Embodiment

In the third embodiment, shown in FIG. 9, the hydraulic system of the second adjustment organ 32 comprises two parts.

The first part comprises a first line 57 putting the first input port 51 into fluid communication with each of the two output ports (54 and 56) intended to communicate with each bag and two clamps (322, 324) placed respectively on each portion of the first line 57 connected to said two output ports (54 and 56).

The second part comprises a second line 58 putting the second output port 52 into fluid communication with each of the two input ports (53 and 55) intended to communicate with each bag, two other clamps (321, 323) placed respectively on each portion of the second line 58 connected to said two input ports (53 and 55).

Description of the Fourth Embodiment

In the fourth embodiment, shown in FIG. 12, the structure of the hydraulic system of the second adjustment organ 32 is different, even if the operation is the same.

Indeed, the second adjustment means 32 comprises two parts.

The first part comprises a first line 57 putting the first input port 51 into fluid communication with each of two output ports (53, 55) intended to communicate with each bag and a first three-way clamp 325 capable of having two alternated positions. The first position is putting the first input port 51 into fluid communication with the third output port 53 at the first bag 11. The second position is putting the first input port 51 into fluid communication with the fifth output port 55 at the second bag 12.

The second part comprises a second line 58 putting the second output port 52 into fluid communication with each of the two input ports (54, 56) intended to communicate with each bag and a second three-way clamp 326 capable of having two following alternated positions. A first position is putting the second output port 52 into fluid communication with the sixth input port 56, at the second bag 12. The second position is putting the second output port 52 into fluid communication with the fourth input port 54, at the first bag 11.

And, for the third and fourth embodiments, the alternating operating mode of loading and unloading is the same. Indeed, the control unit 41 simultaneously controls the clamps (321, 323, 323, 324, 325, 326) of the second adjustment organ 32 so that the two steps are alternated during the operation.

In the first step, the second bag 12 is loaded with liquid while the first bag 11 unloads to the drain 9. In the second step, the first bag 11 is loaded with liquid while the second bag 12 unloads to the drain 9. It should be noticed that during the two phases, the third adjustment organ (33) ensures a substantially continuous flow rate, i.e. the waste is sent to the drain continuously.

The invention also relates to a single-use (or disposable) line for use in the device according to the invention.

In each embodiment, this single-use line comprises at least two bags and four parts of line wherein:
- a first part of line is intended to conduct liquid from the input of the single-use line (80) to one of both bags (11, 12);
- a second part of line is intended to conduct liquid contained in said bag to the output of the single-use bag (80);
- a third part of line is intended to conduct liquid from the input of the single-use line (80) to the other bag (12, 11);
- a fourth part of line intended to conduct liquid contained in the other bag (12, 11) to the output of the single-use line (80).

For the first and second described embodiments, the first and the third parts have a common section connecting both bags.

Indeed, in the first and the second embodiments: the first part of line is constituted by a part of the conduit 80 from the input of the line 80 to the second connection 82 or 821 and by the second branch 82. The second part of the line is constituted by the branch 82 and by a part of the conduit 80 between the connection 821 or 82 and the output of the line to the drain. The third part of the line is constituted by a part of the conduit 80 from the input of the line to the first connection 81 or 811 and by the first branch 81. The fourth part of the line is constituted by the first branch or connection 82 et by the part of the conduit 80 between the first branch or connection 81 or 811 and the output of the line.

In each embodiment, the single-use line comprises a waste line 80 intended to connect the output of the filter 2 to the drain 9, two bags (11, 12) connected each to the waste line 8 and intended to be attached to the treatment device 1, and at least two parts (31b, 33b) of the waste line 8 intended to cooperate respectively with the first adjustment organ 31 and the third adjustment organ 33.

In all the embodiments, the single-use line comprises a drain line 80 intended to connect the filter's output 2 to the drain 9, two bags (11, 12) each connected to the drain line 8 and intended to be attached to the treatment apparatus 1, and at least two parts (31b, 33b) of the drain line 8 intended to work together with the first adjustment organ 31 and the third adjustment organ 33 respectively.

In the first and second embodiments, the single-use line comprises a conduit 80 and at least two connections (81, 82) on the conduit 80.

In the first embodiment, the single-use line comprises another part 32b of the conduit 80 placed between the two connections and intended to work together with the second adjustment organ 32.

In the second embodiment, the single-use line comprises a fourth part (34b) placed on the first branch (81) and intended to work together with the fourth adjustment organ (34).

In the third embodiment, the single-use line comprises an input portion of the line, a drain line 8 and an output portion of the line.

The drain line 8 comprises a first channeling of line 57 intended to put the input portion of the drain line and a port to each bag into fluid communication, the first line being T-shaped, and comprises a second channeling of line 58 intended to put the output portion of the drain line and a second port to each bag into fluid communication, the second line being T-shaped.

In the fourth embodiment, the single-use line comprises an input portion of the line, a drain line 8 and an output portion of the line.

The drain line 8 comprises a first channeling 57 intended to put the input portion of the drain line and a port to each bag into fluid communication, the first channeling comprising a three-way valve with two inputs and one output for the selective connection of the output with one of the two outputs.

The drain line 8 also comprises a second channeling 58 intended to put the output portion of the drain line and a second port to each bag into fluid communication, the second channeling comprising a three-way valve with two inputs and one output for the selective connection of the output with one of the two outputs.

Such a single-use line can be placed before the start of the session on the extracorporeal treatment device. At the end of the session, this line is disconnected, discarded and replaced by a new line for the next session.

The invention also relates to an automatic draining method of the drain line, corresponding to the device according to the invention.

The method comprises two successive alternated phases having the following steps: the continuous flow of a waste through a drain line at a filter output, the first phase, and the second phase successive to and alternating with the first phase.

The first phase comprises the loading of a first container (bag for example) with the waste and the unloading of a second container (bag for example), and the reaching of a first measured threshold weight. The second phase comprises the unloading of a first container of the waste to a drain and the loading of a second container with waste, and the reaching of a second measured threshold weight.

In other words, the automatic draining method can comprise two alternated successive steps:
the first step wherein the load of a first bag (11, 12) with a waste liquid and the unload of a second bag (12, 11) of waste liquid to a drain to the output to the waste line are carried out, this step stopping as soon as one of both bags reaches a first measured weight threshold,
the second step wherein the unload of the first bag (11, 12) to a drain in output of the waste line and the load of the second bag (12, 11) of waste liquid are carried out, this step stopping as soon as one of both bags reaches a second measured weight threshold.

ADVANTAGES OF THE INVENTION

The many advantages obtained by the invention are as follows:
a control of the flow rate of waste going through the drain line is known and controlled,
session duration with the automatic draining device is less than a session duration without automatic draining,
health care personnel no longer have to intervene to carry out the bag changing operation,
the weight of waste extracted from the filter is known and controlled,
the results and qualities of the treatment used according to the state of the art are saved,
the safety level provided by the treatment device is maintained,
hydric balance is maintained,
treatment cost is reduced because two bags are used instead of several bags replaced successively,
the first bag linked to its first gravimetric weighing means and the output portion of the drain line and the drain can be placed not on the device, but placed in a device or a separate part of the treatment device to ensure perfect separation between the device and the patient and the draining: this strengthens the safety of the treatment.

The invention claimed is:

1. A blood treatment device by extracorporeal circulation comprising:
a filter having a primary chamber and a secondary chamber separated by a semi-permeable membrane,
a blood circuit having an arterial line intended to draw blood from a patient, the filter's primary chamber and a venous line intended to return blood to the patient,
a dialysate circuit comprising the filter's secondary chamber and at least one drain line for directing to a drain waste liquid coming from the filter's secondary chamber,
a first bag in fluid communication with the drain line, a second bag in fluid communication with the drain line,
at least one first gravimetric weighing means linked to the first bag,
the drain line including:
one conduit connecting the filter to the drain, said conduit being the only conduit connecting the filter to the drain;
a first branch connecting the first bag to the conduit, said first branch being the only branch connecting the first bag to the conduit;
a second branch connecting the second bag to the conduit, said second branch being the only branch connecting the second bag to the conduit;
said first and second branches being the only elements connected to and in fluid communication with the conduit between the filter and the drain;
the second branch being connected to the conduit upstream of the first branch according to the flow within the conduit;
fluid flow rate adjustment means acting on the drain line comprising:
a first adjustment organ acting upstream of the first and second bags,
a second adjustment organ acting on the conduit between the first branch and the second branch; and
a third adjustment organ acting downstream of the first and second bags,
a control unit linked to the first gravimetric weighing means and to the fluid flow rate adjustment means, the control unit being configured to:

control the first adjustment organ to ensure the presence of a substantially continuous flow rate during the treatment, receive weight signals from the first gravimetric weighing means and, control the fluid flow rate adjustment means to load one of the first and second bags with liquid while the other of the first and second bags unloads liquid, and vice-versa by using first and second threshold values determined by the first gravimetric weighing means wherein the first bag is placed lower than the second bag, such that the control unit is configured to load the first bag in priority with respect to the second bag, and unload the second bag into the first bag by gravity, by opening the second adjustment organ.

2. A device according to claim 1, wherein the control unit is capable of calculating, from the received weight signals, the amount of liquid coming from the filter and entering the drain line.

3. A device according to claim 1, wherein each branch comprises a line with two respective terminal connections.

4. A device according to claim 3, wherein the adjustment means comprises a fourth adjustment organ acting on the first branch between the two connections.

5. A device according to claim 4, wherein the first and fourth adjustment organs are peristaltic pumps and the second and third adjustment organs are valves.

6. A device according to claim 4, wherein the control unit is capable of controlling the flow rate adjustment organs according to the two following alternating steps:

in a first step: the control unit orders the closing of the second adjustment organ, the opening of the third adjustment organ, the activation of the fourth adjustment organ in the bag-to-conduit direction, in a second step: the control unit orders the opening of the second adjustment organ, the closing of the third adjustment organ, the activation of the fourth adjustment organ in the conduit-to-bag direction.

7. A device according to claim 1, wherein each branch comprises a direct connection between the drain line and a bag opening.

8. A device according to claim 1, wherein first and third adjustment organs are peristaltic pumps, and the second adjustment organ is a valve.

9. A device according to claim 8, wherein the control unit is capable of controlling the adjustment organs according to the two following alternating steps:

in a first step: the control unit controls the opening of the second adjustment organ and the stopping of the third adjustment organ to load the second bag and unload the first bag into the drain, in a second step: the control unit controls the opening of the first adjustment organ and the stopping of the third adjustment organ to unload the second bag and load the first bag.

10. A device according to claim 1 or 2, wherein the second adjustment organ comprises a hydraulic system having six ports distributed as follows:

a first input port in fluid communication with the input portion of the drain line to be linked to the filter, a second output port in fluid communication with the output portion of the drain line to be linked to the drain, a third input port and a fourth output port each in fluid communication with the first bag, a fifth input port and a sixth output port each in fluid communication with the second bag.

11. A device according to claim 10, wherein the hydraulic system of the second adjustment organ comprises:

a first line putting the first input port into fluid communication with each of two output ports intended to communicate with each bag, two clamps placed respectively on each portion of the first line connected to said two output ports, and a second line putting the second output port into fluid communication with each of two input ports intended to communicate with each bag, two other clamps placed respectively on each portion of the second line connected to said two input ports.

12. A device according to claim 11, wherein the control unit simultaneously controls the clamps of the second adjustment organ so that the following two steps are alternated during the operation:

in a first step: the second bag is loaded with liquid while the first bag unloads to the drain, in a second step: the first bag is loaded with liquid while the second bag unloads to the drain, and wherein the third adjustment organ ensures a substantially continuous flow rate.

13. A device according to claim 10, wherein the hydraulic system of the second adjustment organ comprises:

a first line putting the first input port into fluid communication with each of two output ports intended to communicate with each bag and a first three-way valve capable of having the two following alternated positions:

first position: putting the first input port into fluid communication with the third output port at the first bag, second position: putting the first input port into fluid communication with the fifth output port at the second bag, a second line putting the second output port into fluid communication with each of two input ports intended to communicate with each bag and a second three-way valve capable of having the two corresponding following alternated positions:

first position: putting the second output port into fluid communication with the sixth input port, at the second bag, second position: putting the second output port into fluid communication with the fourth input port, at the first bag.

14. A device according to claim 13, wherein the control unit simultaneously controls the clamps of the second adjustment organ so that the following two steps are alternated during the operation:

in a first step: the second bag is loaded with liquid while the first bag unloads to the drain, in a second step: the first bag is loaded with liquid while the second bag unloads to the drain, and wherein the third adjustment organ ensures a substantially continuous flow rate.

15. A device according to claim 1 comprising a second gravimetric weighing means linked to the second bag and linked to the control unit.

16. A device according to claim 1 or 15, wherein the control unit is capable of calculating the amount of fluid coming from the filter and entering the drain line from the weight signals received from the first or second gravimetric weighing means or from both the first and second gravimetric weighing means.

17. A device according to claim 1 or 15, wherein the control unit is capable of:
- receiving weight information from the first or second gravimetric weighing means or from both the first and second gravimetric weighing means,
- calculating the actual fluid flow rate coming from the filter and comparing it with a required flow rate, and
- controlling the actual fluid flow rate by the adjustment means to approach the required fluid flow rate coming from the filter.

18. A device according to claim 1 or 15, wherein the control unit is capable of:
- receiving weight information from the first or second gravimetric weighing means or from both the first and second gravimetric weighing means,
- independently determining the filling status of each bag,
- controlling, from the filling status of each bag, an alternated and successive bag loading and unloading procedure.

19. A device according to claim 15, wherein the control unit is capable of activating a control procedure comprising the following two alternated steps:
- in a first step: controlling the actual flow rate of the adjustment means according to the required flow rate profile and the weight information coming from at least the first gravimetric weighing means,
- in a second step: controlling the actual flow rate of the adjustment means according to the required flow rate profile and the weight information coming from the first and second gravimetric weighing means.

20. A device according to claim 19, wherein the control unit is capable of activating a control procedure comprising two alternated steps and in that the control of the actual flow rate of the adjustment means during the first step is also performed according to the weight information of the second gravimetric weighing means.

21. A device according to claim 1 or 15, wherein the control unit is capable of:
- receiving weight information from the first gravimetric weighing means and/or from the second gravimetric weighing means,
- detecting the maximum and minimum threshold values for each of the bags $P_{1mini}$, $P_{1maxi}$, $P_{2mini}$, $P_{2maxi}$,
- controlling from the threshold values a bag loading and unloading procedure according to the following steps:
- loading of one bag and unloading of the other bag,
- detection of a limit threshold,
- unloading of one bag and loading of the other bag,
- detection of another limit threshold.

22. An automatic draining method run on a device according to claim 1 comprising:
- the step of controlling the first adjustment organ to ensure the presence of a substantially continuous flow rate during the treatment, and two alternated successive steps:
- a first step wherein the first bag is loaded, only through the first branch, with a waste liquid and the second bag is unloaded, only through the second branch, of waste liquid to the drain in output of the drain line, this step stopping as soon as one of the first and second bags reaches a first measured weight threshold,
- a second step wherein the first bag is unloaded, only through the first branch, of waste liquid to the drain in output of the drain line and the second bag is loaded, only through the second branch, of waste liquid, this step stopping as soon as one of the first and second bags reaches a second measured weight threshold,
- wherein all the fluid coming from the first adjustment organ is conveyed to the third adjustment organ and passes exclusively through the conduit between the filter and the drain.

23. A method according to the claim 22 comprising the step of calculating, from the received weight signals, the amount of liquid coming from the filter and entering the drain line.

24. A method according to the claim 22 wherein the apparatus comprises a third adjustment organ acting downstream of the two bags and wherein the method comprises the control by the control unit of the adjustment organs according to the two following alternating steps:
- in a first step: the opening of the second adjustment organ and the stopping of the third adjustment organ to load the second bag and unload the first bag into the drain,
- in a second step: the opening of the first adjustment organ and the stopping of the third adjustment organ to unload the second bag and load the first bag.)

25. A method according to the claim 22, wherein the device comprises a second gravimetric weighting means linked to the second bag and linked to the control unit, and wherein the method comprises following steps: calculating the amount of fluid coming from the filter and entering the drain line from the weight signals received from the first gravimetric weighing means and/or from the second gravimetric weighing means.

26. A method according to the claim 22, wherein the device comprises a second gravimetric weighting means linked to the second bag and linked to the control unit, and wherein the method comprises following steps:
- receiving weight information from the first gravimetric weighing means, the second gravimetric weighing means, or both the first and second gravimetric weighing means,
- calculating the actual fluid flow rate coming from the filter and comparing it with a required flow rate,
- controlling the actual fluid flow rate by the adjustment means to approach the required fluid flow rate coming from the filter.

27. A method according to the claim 22, wherein the device comprises a second gravimetric weighting means linked to the second bag and linked to the control unit, and wherein the method comprises following steps:
- receiving weight information from the first gravimetric weighing means, the second gravimetric weighing means, or both the first and second gravimetric weighing means,
- independently determining the filling status of each bag,
- controlling, from the filling status of each bag, an alternated and successive bag loading and unloading procedure.

28. A method according to the claim 22, wherein the device comprises a second gravimetric weighting means linked to the second bag and linked to the control unit, and wherein the method comprises following steps:
- in a first step: controlling the actual flow rate of the adjustment means according to the required flow rate profile and the weight information coming from at least the first gravimetric weighing means,
- in a second step: controlling the actual flow rate of the adjustment means according to the required flow rate profile and the weight information coming from the first and second gravimetric weighing means.

29. Method according to the claim 22, wherein the device comprises a second gravimetric weighting means linked to the second bag and linked to the control unit, and wherein the method comprises following steps:

receiving weight information from the first gravimetric weighing means, the second gravimetric weighing means, or both the first and second gravimetric weighing means, detecting the maximum and minimum threshold values for each of the bags $P_{1mini}$, $P_{1maxi}$, $P_{2mini}$, $P_{2maxi}$, controlling from the threshold values a bag loading and unloading procedure according to the following steps:

loading of one bag and unloading of the other bag, detection of a limit threshold, unloading of one bag and loading of the other bag, detection of another limit threshold.

\* \* \* \* \*

UNITED STATES PATENT AND TRADEMARK OFFICE
CERTIFICATE OF CORRECTION

PATENT NO.        : 7,588,722 B2                                      Page 1 of 1
APPLICATION NO.   : 10/873191
DATED             : September 15, 2009
INVENTOR(S)       : Jacques Chevallet It is certified that error appears in the above-identified patent and that said Letters Patent is hereby corrected as shown below:

In claim 23, column 16, line 5, "to the claim" should read --to claim--.

In claim 24, column 16, line 8, "to the claim" should read --to claim--.

In claim 24, column 16, line 18, "bag.)" should read --bag.--.

In claim 25, column 16, line 19, "to the claim" should read --to claim--.

In claim 25, column 16, line 20, "weighting" should read --weighing--.

In claim 26, column 16, line 27, "to the claim" should read --to claim--.

In claim 26, column 16, line 28, "weighting" should read --weighing--.

In claim 27, column 16, line 41, "to the claim" should read --to claim--.

In claim 27, column 16, line 42, "weighting" should read --weighing--.

In claim 28, column 16, line 53, "to the claim" should read --to claim--.

In claim 28, column 16, line 54, "weighting" should read --weighing--.

In claim 29, column 16, line 66, "to the claim" should read --to claim--.

In claim 29, column 16, line 67, "weighting" should read --weighing--.

Signed and Sealed this

Third Day of November, 2009

David J. Kappos
*Director of the United States Patent and Trademark Office*